United States Patent [19]

O'Brien et al.

[11] Patent Number: 4,904,605
[45] Date of Patent: Feb. 27, 1990

[54] METHOD AND APPARATUS FOR RESIDENTIAL WATER TEST KIT

[75] Inventors: Mark R. O'Brien, Glastonbury; Mark S. Barre, Stamford; Michael S. Newton, Durham, all of Conn.

[73] Assignee: Cuno, Inc., Meriden, Conn.

[21] Appl. No.: 209,702

[22] Filed: Jun. 20, 1988

[51] Int. Cl.⁴ .............................................. G01N 31/22
[52] U.S. Cl. ...................................... 436/169; 422/50; 422/55; 422/56; 422/57; 422/58; 422/61; 436/79; 436/125; 436/163
[58] Field of Search ................. 436/79, 86, 169, 170, 436/125, 163; 422/61, 56, 57, 50, 55, 58

[56] References Cited

U.S. PATENT DOCUMENTS

| | | | |
|---|---|---|---|
| 1,986,403 | 1/1935 | Lehmkahl | 436/125 |
| 3,006,735 | 10/1961 | Jordan | 436/79 |
| 3,381,572 | 5/1968 | Tuwiner | 422/55 |
| 3,443,903 | 5/1969 | Haack | 438/86 |
| 3,447,904 | 6/1969 | Rupe | 436/169 |
| 3,510,263 | 5/1970 | Hach | 436/125 |
| 4,125,376 | 11/1978 | Razulis | 422/56 |
| 4,438,067 | 3/1984 | Siddigi | 436/169 |

FOREIGN PATENT DOCUMENTS 2422954 12/1979 France ........................ 422/56

OTHER PUBLICATIONS

Devine, J., "A Chloride-Testing Paper for Clinical Use by Untrained Persons", Medical J. of Australia, Aug. 25, 1951, p. 264.

Primary Examiner—Christine M. Nucker
Assistant Examiner—Jill Johnston
Attorney, Agent, or Firm—Weingram & Zall

[57] ABSTRACT

The present invention relates, generally, to an apparatus and method for water testing and, more particularly, to a simple dipstick type method for use in comparison with a color chart and suggested courses of action to correct deficiencies in water quality. Briefly stated, a detailed color chart is attached to the side of a container having a plurality of dipsticks contained therein. Each dipstick has disposed thereon a plurality of pads, the total number corresponding to the number of characteristics of the water to be tested. Additionally disclosed is a course of corrective action which may be undertaken by the unskilled user thereby greatly simplifying the process by reducing it to its simplest factors.

12 Claims, 2 Drawing Sheets

FIG-1
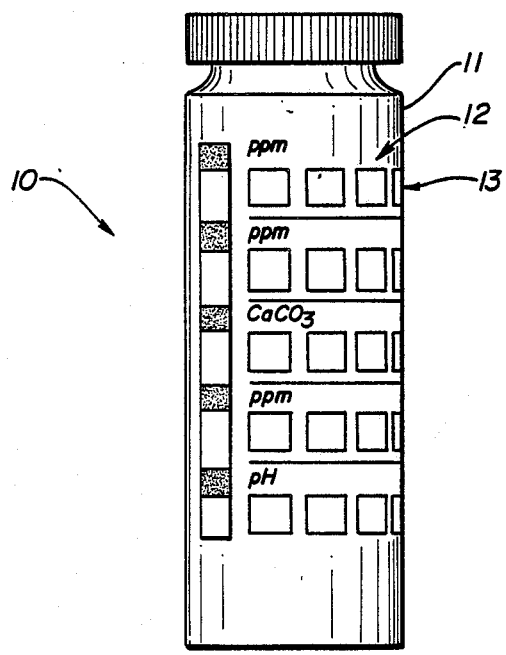
FIG-3
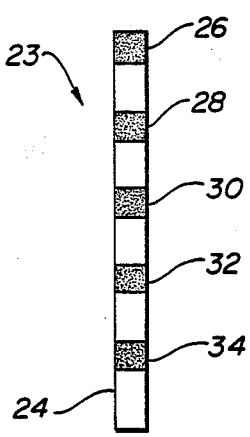

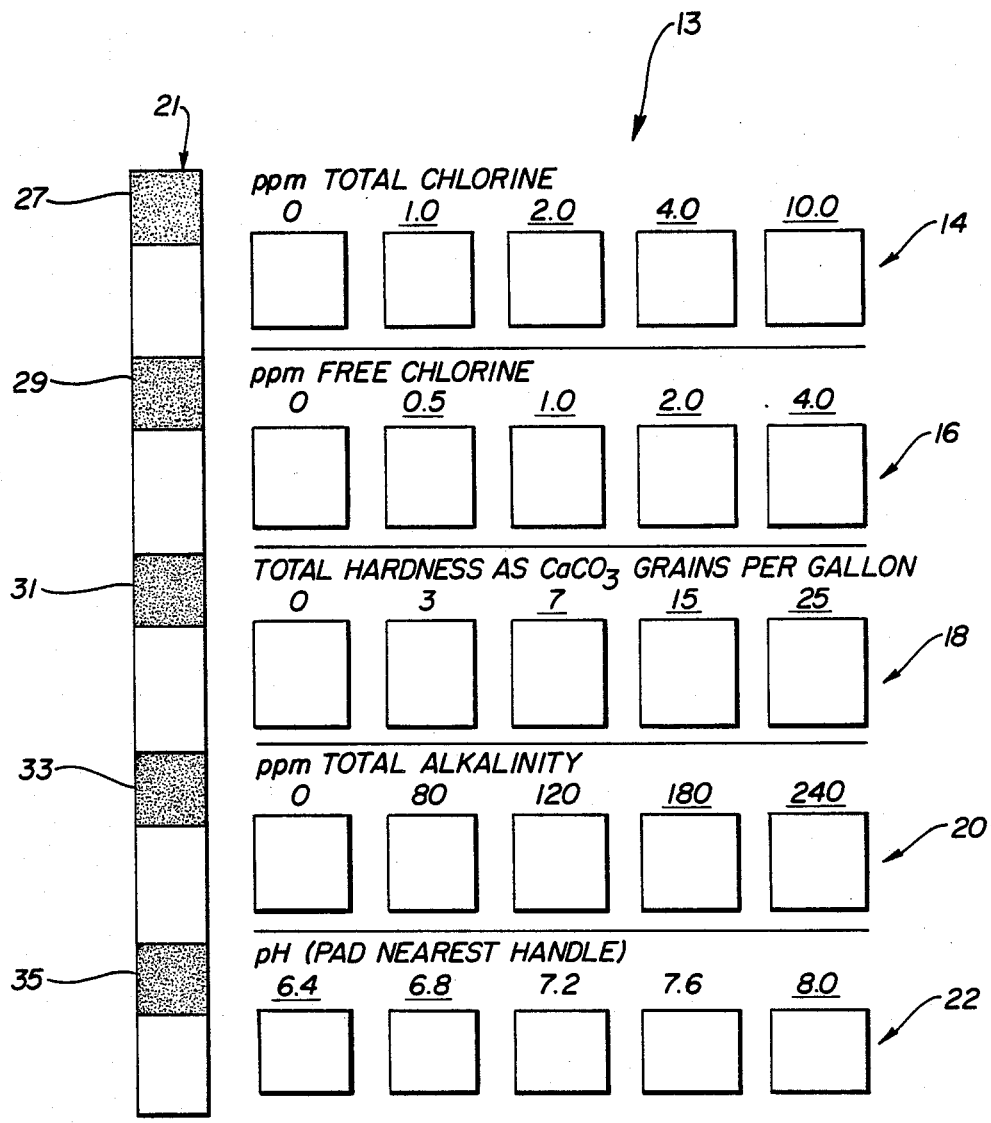

METHOD AND APPARATUS FOR RESIDENTIAL WATER TEST KIT

BACKGROUND OF THE INVENTION

This invention relates, generally, to water testing and more particularly to a method and device for the testing of residential or domestic water supplies at the point of use and to recommend a course of action for the correction of certain common domestic water problems.

Ever since domestic plumbing systems have come into use in this country, there has been a need to evaluate the quality of water in order to ascertain the actual potential for damage to plumbing fixtures and the like. More recently, with the aging of water supply systems in many municipalities, the acute need for testing and corrective measures has increased. Further, there is also the need to evaluate the quality of water in order to maintain certain taste and health standards.

Heretofore, testing procedures were either required to be done by professionals who then made specific recommendations or were accomplished via testing kits. Laboratory testing analysis by an outside service is expensive and takes an appreciable amount of time before results can be obtained. Test kits were and are typically expensive, cumbersome and/or difficult to utilize, see for example, U.S. Pat. No. 4,195,059 to Whitcher et al.

Typically, these tests kits attempted to determine appropriate levels of substances or properties such as acidity, total chlorine, free chlorine, total hardness as $CaCO_3$, total alkalinity or pH.

A number of patents have issued for the specific purpose of testing for one or more of these substances or properties for different purposes or reasons. U.S. Pat. No. 1,967,557 to John relates to a device for testing acidity in oral secretions. U.S. Pat. No. 3,006,735 to Jordan relates to a quick dip indicator which includes a carrier absorptive to the liquid being analyzed. The carrier has a plurality of spaced areas, each of which contains a substance color responsive to different concentrations of a particular ion being made. To obtain a measurement with the indicator, the indicator is dipped into the liquid and immediately removed therefrom. The concentration of ions in the liquid is shown by a color change in the spaced areas. U.S. Pat. No. 3,963,442 to Bullard et al. relates to a colorimetric indicator. The drawings illustrate a dipstick having a plurality of "tabs" which are bonded to the dipstick. U.S. Pat. No. 4,195,059, previously mentioned, utilizes containers having color indicia thereon. U.S. Pat. No. 4,409,182 to Macklem utilizes a tube having on it a plurality of plastic components. Finally, U.S. Pat. No. 4,092,115 to Rupe et al. utilizes a dipstick type apparatus for detecting free available chlorine in a liquid.

All of the above-mentioned devices or tests are inadequate for true "home-testing kits" in a number of ways. In particular, reading and hence analysis is difficult in that it requires comparison to charts which are not, generally, readily available. Further, none allow for a total of the five important tests enumerated above, i.e. total chlorine, free chlorine, total hardness as $CaCO_3$, total alkalinity and pH to be tested simultaneously. Further, none of the above-mentioned devices allow the results of such tests to be easily compared with a chart or other suitable information source to instruct the user as to the appropriate procedures or devices to be utilized to correct any problems indicated by the tests.

Finally, another device which is utilized to test domestic water is found in a product entitled "Marathon Pool and Spa Triple Dip Strip" distributed by Marathon Organization, Allentown, Penna. 18104. This device utilizes a dipstick having three pads thereon for testing pH, total alkalinity and free chlorine. The dipstick is inserted into the pool or spa water and then compared to vertically oriented color charts on the container in which the dipsticks are packaged. Due to the orientation of the color chart, only one pad is capable of being compared to the color chart at any given time and the color chart or the dipstick must be moved coaxially in order to compare the specific colors with the actual shade of each pad. Moreover, no corrective action is suggested other than the addition of chlorine.

Accordingly, it is an object of the present invention to provide a water test apparatus which is inexpensive to manufacture. It is still a further object of the present invention to produce a water testing apparatus which is simple to manufacture and utilize.

It is yet another object of the present invention to produce water test apparatus wherein the results are readily correlated with a system of corrective measures which are readily usable and understandable by the end user.

Another object of the present invention is to produce a water test apparatus which allows the user to compare the quality of water after corrective measures have been taken with the quality of water prior to the institution of corrective measures.

It is still a further object of the present invention to provide a method for performing water test procedures which is simple to utilize. It is yet another object of the present invention to produce a water test apparatus which is effectively "goof-proof" so that the unskilled user can take the correct and appropriate corrective action.

Still another object of the present invention is to produce a water test apparatus which is compact, has no moving parts and which is completely safe to use.

It is another object of the present invention to produce a water test apparatus which produces immediate results without the need for extensive or delayed testing.

Yet another object of the present invention is to produce a water test apparatus which permits water quality to be individually adjusted at different locations, for example, the bathroom, kitchen, exterior faucet, washing machine and the like.

DESCRIPTION OF THE DRAWINGS

Reference may be now had to the accompanying drawings in which:

FIG. 1 is an elevational view of the container including the label thereon for use with the present device;

FIG. 2 is a more detailed view of the label shown in FIG. 1; and

FIG. 3 is an elevational view of the water test dipstick utilized in the present invention.

DESCRIPTION OF THE PREFERRED EMBODIMENT

Reference may be now had to FIG. 1. Illustrated are the test kit components, shown generally at 10. The kit 10 is comprised of a container 11 having disposed on the exterior thereof a label 12. The label 12, preferably, has abbreviated operating instructions, although it is obvious that more detailed and comprehensive instructions (not shown) may be included with the sale of the entire kit 10. Also disposed on the label 12 is a color comparison chart 13 which is shown in much more detail in FIG. 2. Chart 13 indicates the characteristics which are preferably to be tested. These characteristics are total chlorine in parts per million (ppm), free chlorine in ppm, total hardness ($CaCO_3$) as grains per gallon, total alkalinity as ppm, and pH. It is to be understood, however, that a greater or lesser number of characteristics may be tested as well as different characteristics entirely. However, it has been found that these characteristics are the characteristics which most often affect the quality of water and, more particularly, the aesthetic qualities, e.g. taste, color and smell. Accordingly, while taste and smell are obviously very important in a kitchen faucet for drinking purposes, hardness is not as important. Similarly, hardness is extremely important with respect to washing the dishes, clothes and the like as well as use in vitrous china and porcelain such as bath tubs, sink basins and the like.

Referring to FIG. 2, chart 13 has row 14 specifically for the purpose of determining total chlorine in parts per million and is printed in color from plain white for the box having the value of "0" and various shades of purple with the darkest being for the block having the value of "10.0". Similarly, row 16 tests free chlorine in parts per million with block 0 being yellow, block 0.5 being slightly tan and block 1.0 through 4.0 being three different shades of purple from lightest to darkest respectively. Row 18 is utilized for testing the total hardness of the water as $CaCO_3$ in grains per gallon. Block 0 is a dark or kelly green type of color, block 3 is a dark brown with block 7 being a lighter shade of brown and graduating to block 25 which is the lightest shade of brown. Row 20 tests for total alkalinity in parts per million with block 0 being a light green and block 240 being a moderate dark green with the intermediate blocks in intermediate shades therebetween. Row 22 is utilized to indicate pH with block 6.4 being medium yellow with the intermediate blocks increasing in darkness to block 8.0 which is light red in color.

Disposed to the left of chart 13 is a vertical outline 21 of a dipstick (as shown in FIG. 3). The vertical outline 21 shows five distinct areas 27, 29, 31, 33 and 35 corresponding with the five different areas on dipstick 23 for use in testing for the five different characteristics of the water. Obviously, should the number of characteristics being tested increase or decrease, then the number of areas 27 through 35 would, of course, correspondingly change, as well as rows 14 through 22. Vertical outline 21 is utilized to indicate orientation of the dipstick 23 with respect to chart 13 when comparing the areas on the dipstick to the rows.

Referring to FIG. 3, dipstick 23 is comprised of a base 24 having five spaced apart pads thereon, 26, 28, 30, 32 and 34. Each pad 26-34 is utilized to test for a specific characteristic corresponding to the characteristics disposed on chart 13. Accordingly, pad 34 which is disposed nearest the handle is utilized to test the pH and hence is to be compared with row 22 on chart 13 (after immersion in the water to be tested as described more fully below). Accordingly, the legend on row 22 indicates that the pad nearest the handle has to be utilized. Accordingly, this therefore orients the remainder of dipstick 23 with the various rows 14–20 on chart 13.

Pads 26-34 are comprised of liquid absorption type materials which are readily available, see for example U.S. Pat. No. 4,092,115 to Rupe et al., incorporated herein by reference.

Accordingly, to test water and to make corrective actions, the following procedure has been found to be most effective. It has been found that these procedures are easy and simple to follow by the user and minimize any chance for error either in the testing process or in any follow-up corrective actions.

TEST INSTRUCTIONS

Step 1: Remove empty sample bottle from test kit. Run cold tap water for five minutes. Fill sample bottle with cold water.

Step 2: Remove one dipstick or test strip 23 from labeled bottle 11. Firmly reclose bottle.

Step 3: Fully immerse test strip 23 in sample bottle for one second.

Step 4: Hold or lay the test strip 23 flat for 30 seconds. After 30 seconds, compare the 3 pads closest to the strip handle 34, 32 and 30 (pH, Total Alkalinity, and Total Hardness) to the bottom three color chart rows 22, 20 and 18 on the bottle 11. Match each of the three pad colors to the closest corresponding color in the aligned row on the chart. Note the number above the color and record these.

Step 5: Place the bottom two pads 27 and 29 (Free Chlorine, Total Chlorine) under running cold water for 15 seconds. NOTE—If running water is not available, re-dip the bottom two pads (Free Chlorine, Total Chlorine) in the sample bottle. Move the strip back and forth vigorously for 30 seconds.

Step 6: Remove test strip 23 and compare to the top two color chart rows 14,16, finding the closest colors. Note the figure directly above the color chart on the bottle that is closest to the color on your pad, and record that number.

Step 7: To calculate your chloramine level, subtract your Free Chlorine reading from your Total Chlorine reading. This will give you your level of chloramine.

Preferably, the numbers contained on chart 13 which are underlined are printed in red (as distinct from black for all other numbers). The purpose for this is to indicate to the user that problem levels are present when colors match these specific areas.

Thereafter, appropriate instructions for the user would tell the user how to analyze the results obtained in the above recited test.

ANALYZING THE RESULTS

Compare the recorded numbers with the following standards: (Problem levels as mentioned are indicated on the bottle in Red numbers)

1. Total Chlorine. Any number over 1.0 ppm (parts per million) will affect the taste and odor of water. Any reading under 1.0 ppm is considered moderate.

2. Free Chlorine. Anything over 0.5 ppm (parts per million) is considered excessive and will affect the taste of water as well as food and beverages prepared with this water.

3. Total Hardness. Any reading from 3 grains per gallon (gpg) to 7 gpg is considered moderately hard, from 7.0 gpg to 15.0 gpg is hard and above 15.0 gpg very hard. Moderately hard and very hard water means your water can cause scaling in water fixtures, hot water systems, and pipes. This hard water scale can cause clogging of pipes and fixtures, leaking faucets, and hot water system burn out. Scale build up can shorten the life of hot water systems and cause them to operate at less than peak efficiency.

4. Alkalinity. A high alkalinity reading combined with a high hardness reading means your tap water is more apt to scale than water with high hardness and low alkalinity. It also causes an acrid taste to water.

5. Acidity. A pH reading of 6.4 to 6.8 means acidic water which can cause corrosion of pipes, valves and fittings. This corrosion can release copper and lead into your water supply. A pH above 8.0 combined with high alkalinity and hardness can cause scaling problems. (see Total Hardness).

6. Chloramine. Any value over 1 ppm (parts per million) will affect the taste and odor of water as well as food and beverages prepared with this water.

Finally, once the water has been properly tested and the results of the test are known to the user, a course of action is suggested. This course of action has been found to be easily understood when placed into chart form as indicated below.

It is to be noted that the filter numbers such as, for example, PP01002, PP01105 and PP02000 are model numbers given to specific filters manufactured and sold by the assignee of the present invention.

Further, this cataloguing will indicate to the user that previously taken corrective measures such as filters and the like are no longer operative and should be repaired or replaced. It is to be understood, however, that it may be possible to compare the user's written numbers corresponding to different values rather than retention of the actual dipstick 23.

Having thus described the present invention in detail, it is to be understood that the foregoing description is not intended to limit the spirit and scope thereof. What is desired to be protected by Letters Patent is set forth in the appended claims.

What is claimed is:

1. A method of testing for a plurality of contaminants in water, comprising the steps of:
 (a) providing an elongated test strip having thereon a plurality of reagent test pads along its length, each test pad containing a reagent responsive to a different contaminant in water and indicating a concentration of its respective contaminant by its color characteristic;
 (b) immersing the test strip and the reagent test pads into the water for a period of time;
 (c) removing the test strip from the water;
 (d) providing a comparison chart having thereon a

SOLUTION CHART

| Problem | Whole Home Filter installed on the main water supply line will | Undersink Point of use filter installed under the sink. | End-of-Faucet Point of use filter installed on the end of a faucet. | Icemaker Small filter used to improve the taste of coffee and any other beverage drunk with ice. | How to Solve the Problem |
|---|---|---|---|---|---|
| Total Chlorine Free Chlorine, Chloramine | — | PP010002 | PP01105 | PP02000 | The recommended filters all have activated granulated carbon in their cartridges. These filters also remove dirt, rust, and sediment, to provide clear, good-tasting water. |
| Hardness, Alkalinity, pH (red numbers greater than 8.0) | PP01101 | Whole house solution recommended rather than under sink. | — | PP02000 | At very high levels of hardness (above 15 grains) and/or alkalinity, a softener may be required. If a softener is installed and there is a high hardness and/or alkalinity reading on the test strip, the softener may not be functioning correctly. |
| pH (red numbers less than 7.2) | PP01101 | Whole house solution recommended rather than under sink. | — | PP02000 | The filter cartridge inhibits acid water corrosion by applying a protective coating to pipes and water heating appliances. |
| Dirt, Rust & Sediment | PP01101 | PP01002 (also removes bad tastes and odors) | PP01106 (also removes bad tastes and odors) | PP02000 (also removes bad tastes and odors, and inhibits scale build-up) | The filters remove dirt, rust and sediment to protect pipes, valves, and fixtures and give clean, good tasting water. |

It is preferred that once a particular test has been accomplished, the dipstick 23 should be marked with the appropriate date and location of sampling. Thereafter, the user can compare subsequent tests to determine any changes in the characteristics of the water over a period of time or as a result of an corrective measures taken. Accordingly, the user is readily informed as to whether the measures are effective or ineffective or whether under or overcompensation has taken place.

vertical outline of said test strip utilized to indicate the orientation of the test strip with respect to the comparison chart and a plurality of standard value rows,
 each of said rows having at least one colored standard area, all of said areas in each row corresponding to a color characteristic for different concentration standards of the same respective contaminant in water; and a concentration indicator associated with each area for quantitatively indicating the concentration standard of the respective contaminant;

wherein the vertical outline and rows are arranged so that upon positioning of the test strip on the vertical outline each test pad substantially aligns with a test row, each test row corresponding to the concentration standards for the respective contaminant it is aligned with, thereby facilitating test comparisons between the respective test pad and color area;

(e) positioning the test strip on the vertical outline of the comparison chart;

(f) comparing each of the test pads with its associated test row to substantially match the color of the respective test pad with one of the color test areas of the respective associated row, the concentration indicator associated with the area indicating the measured concentration of the respective contaminant substance in the water.

2. The method of claim 1, further comprising:

(g) providing a corrective course chart which references corrective courses of action for controlling a contaminant in the water, indexed against the concentration in the water of the respective contaminant;

(h) locating the measured concentration of the respective contaminant substance on the corrective course chart to thereby indicate a corrective course of action.

3. The method of claim 1, wherein the test pads are adapted for testing pH, total alkalinity, total hardness, free chlorine and total chlorine of the water.

4. The method of claim 3, wherein step (f) comprises comparing each of the test pads for testing pH, total alkalinity and total hardness with its associated test row.

5. The method of claim 4, further comprising after step (f):

(g) immersing a portion of the test strip containing the test pads for testing free chlorine and total chlorine into the water for an additional period of time;

(h) removing the test strip from the water;

(i) positioning the test strip on the test strip column;

(j) comparing the test pads for testing free chlorine and total chlorine with their associated test row to substantially match the color of the respective test pad with one of the colored standard areas of the respective associated row, the concentration indicator associated with the area indicating the measured concentration of the respective contaminant substance in the water; and (k) determining the concentration indicator for free chlorine and total chlorine; and (l) subtracting the free chlorine indicator from the total chlorine indicator to thereby determine the chloramine concentration.

6. A kit for testing for a plurality of contaminants in water comprising:

(a) an elongated test strip having thereon a plurality of reagent test pads along its length, each test pad containing a reagent responsive to a different contaminant in the water and indicating a concentration of its respective contaminant by its color characteristics;

(b) providing a comparison chart having thereon a vertical outline of said test strip utilized to indicate the orientation of the test strip with respect to the comparison chart and a plurality of standard value rows, each of said rows having at least one colored standard area, all of said areas in each row corresponding to a color characteristic for different concentration standards of the same respective contaminant in water; and a concentration indicator associated with each area for quantitatively indicating the respective concentration standard of the respective contaminant;

wherein the vertical outline and rows are arranged so that upon positioning of the test strip on the vertical outline each test pad substantially aligns with a standard row, each standard row corresponding to the concentration standards of the respective contaminant of the pad it is aligned with, thereby facilitating test comparisons between the respective test pad and color area.

7. The kit of claim 6, further comprising an instruction sheet.

8. The kit of claim 7, further comprising a corrective course chart which references corrective courses of action for controlling a contaminant in the water indexed against the concentration in the water of the respective contaminant substance.

9. The kit of claim 6, further comprising a container for housing the test strip.

10. The kit of claim 9, wherein the container has thereon the comparison chart.

11. The kit of claim 10, wherein the container is elongated, and the test strip column is coaxial with the vertical axis.

12. The kit of claim 11, wherein the container is cylindrical.

* * * * *